United States Patent [19]

Prockop et al.

[11] Patent Number: 5,593,859
[45] Date of Patent: Jan. 14, 1997

[54] SYNTHESIS OF HUMAN PROCOLLAGENS AND COLLAGENS IN RECOMBINANT DNA SYSTEMS

[75] Inventors: Darwin J. Prockop, Philadelphia; Leena Ala-Kokko, Andalusia, both of Pa.; Andrzej Fertala, Voorhees, N.J.; Aleksander Sieron, Conshohocken, Pa.; Kari I. Kivirikko, Oulu, Finland; Amy Geddis, Philadelphia, Pa.; Taina Pihlajaniemi, Oulunsalo, Finland

[73] Assignee: Thomas Jefferson University, Philadelphia, Pa.

[21] Appl. No.: 211,820

[22] Filed: Aug. 11, 1994

Related U.S. Application Data

[63] Continuation-in-part of Ser. No. 37,728, filed as PCT/US92/09061, Oct. 22, 1992, Pat. No. 5,405,757, which is a continuation of Ser. No. 780,899, Oct. 23, 1991, abandoned.

[51] Int. Cl.$^6$ ............................... C12N 1/19; C12N 5/10; C12N 15/12; C07K 14/78
[52] U.S. Cl. .................. 435/69.1; 435/172.3; 435/240.2; 435/254.2; 530/356
[58] Field of Search ............................... 435/69.1, 240.2, 435/172.3, 70.3, 320.1, 69.8, 240.1; 530/356, 23.5, 24.1

[56] References Cited

U.S. PATENT DOCUMENTS 5,045,449  9/1991  Ala-Kokko et al. .................. 435/6

OTHER PUBLICATIONS

Hamalainen, L. et al., *J. Biol. Chem.* 260(2): 720–725 (1985).

Ahmad et al., "A stop codon in the gene for type II procollagen (COL2A1) causes one variant of arthro–ophthalmapathy (the Stickler syndrome)" *Am. J. Hum. Genet.*, 47:A206, 1990.

Ala–Kokko et al., "Single base mutation in the type II procollagen (COL2A1) as a cause of primary osteoarthritis associated with a mold chondrodysplasia" *Proc. Natl. Acad. Sci. U.S.A.*, 87:6565–6568, 1990.

Anderson et al., "Spondyloepiphyseal Dysplasia Congenita: Genetic Linkage to Type II Collagen (COL2A1)" *Am. J. Hum. Genet.*, 46:896–901, (1990).

Aulthouse et al., "Expression of the Human Chondrocyte Phenotype In Vitro.," In Vitro *Dev. Biol.*, 25:659–668, 1989.

Bruckner and Prockop, "Proteolytic Enzymes as Probes for the Triple–Helical Conformation of Procollagen," *Anal. Biochemistry* 110:360, 1981.

Elima and Vuorio, "Expression of mRNAs for collagens and other matrix components in dedifferentiating and redifferentiating human chondrocytes in culture," *FEBS Lett.*, 258:195–198, 1989.

Cheah et al., "Identification and characterization of the human type II collagen gene (COL2A1)" *Proc. Natl. Acad. Sci. USA*, 82:2555–2559, 1985.

Francomano et al., "The Stickler Syndrome: Evidence for Close Linkage to the Structural Gene for Type II Collagen," *Genomics*, 1:293–296, 1987.

Prockop and Kivirikko, "Heritable Diseases of Collagen," *N. Engl. J. Med.*, 311:376–386, 1984.

Knowlton et al., "Genetic Linkage Analysis of Hereditary Arthro–Ophthalmopathy (Stickler Syndrome) and the Type II Procollagen Gene," *Am. J. Hum. Genet.*, 45:681–688, 1989.

Knowlton et al., "Genetic Linkage of a Polymorphism in the Type II Procollagen Gene (COL2A1) to Primary Osteoarthritis Associated with Mild Chondrodysplasia," *N. Engl. J. Med.*, 322:526–530, 1990.

Law et al., "A Stable Bovine Papillomavirus Hybrid Plasmid That Expresses a Dominant Selective Trait," *Molec. Cell Biol.*, 3:2110–2115, 1983.

Lee et al., "Identification of the Molecular Defect in a Family with Spondyloepiphyseal Dysplasia," *Science*, 244:978–980, 1989.

Greenspan et al., "High Levels of Expression of Full Length Human Pro–α2 (V) Collagen cDNA in Pro–α2(V)–Deficient Hamster Cells", *J. Biol. chem.*, 264:20683–20687 (1989).

Palotie et al., "Predisposition to Familial Osteoarthriosis Linked to Type II Collagen Gene," *The Lancet*, I:924–927, 1989.

Tiller et al., "Tandem duplication within a type II collagen gene (COL2A1) exon in an individual with a spondyloepiphyseal dysplasia," *Proc. Natl. Acad. Sci. U.S.A.*, 87:3889–3893, 1990.

Vissing et al., "Glycine to Serine Substitution in the Triple Helical Domain of Pro–α1 (II) Collagen Results in a Lethal perinatal Form of Short–limbed Dwarfism," *J. Biol. Chem.*, 264:18265–18267, 1990.

Bornstein et al., "Regulatory elements in the first intron contributed to transcriptional control of the human α1 (I) collagen gene," *Proc. Natl. Acad Sci. U.S.A.*, 84:8869–8873, 1987.

Ala–Kokko et al., "Expression of the Human Type II Procollagen Gen in Mouse NIH 3T3 Cells by Use of a Vector Containing the Promoter Region the First Exon and The First Intron of the Pro–Alpha–II chain for Human Type I Procollagen" *Matrix*, 10(4):234, Jun. 13–16, 1990.

Olsen et al., "High Levels of Expression of a Minigene Version of the Human Proα1 (I) Collagen Gene in Stably Transfected Mouse Fibroblasts," *J. Biol. Chem.*, 266:1117–1121, 1991.

(List continued on next page.)

*Primary Examiner*—Dian C. Jacobson
*Attorney, Agent, or Firm*—Albert P. Halluin, Esq.; Pennie & Edmonds

[57] ABSTRACT

The invention is transfected cells, substantially all of which contain at least one human collagen gene and express fibrillar collagen molecules derived using methods for synthesizing collagen and collagen fibrils in said cell lines, and methods for treatment of disorders in humans using said collagen derived from said stable cell lines.

23 Claims, 5 Drawing Sheets

OTHER PUBLICATIONS de Wet et al., "Synthesis of a Shortened Pro–α2 (I) Chain and Decreased Synthesis of Pro–α2 (I) Chains in a Proband with Osteogenesis Imperfecta," *Journal of Biological Chemistry*, 258:7721–7728, 1983.

Laemmli, U. K., "Cleavage of Structural Proteins during the Assembly of the Head of Bacteriophage T4," *Nature*, 227:680–685, 1970.

Ala–Kokko et al., "Expression of a Human Cartilage Procollagen Gene (CL2A1) in Mouse 3T3 Cells," *J. of Biol. Chem.*, 266: 14175–14178, 1991.

Prockop et al., "Expression of Type I Procollagen Genes" in Cell and Molecular Biology of Vertebrate Hard Tissues, 142–160 (1988).

Fertala et al., "Synthesis of Recombinant Human Procollagen II in a Stably Transfected Tumour Cell Line (HT1080)", *Biochem J.* 298: 31–37 (1994).

Dickson et al., "Nuclease S1 Mapping of a Homozygous Mutation in the Carboxyl–Propeptide–Coding Region of the proα2 (I) Collagen Gene in a Patient With Osteogenesis Imperfecta", *PNAS USA* 81: 4524–4528 (1984).

Peltonen et al, "Thermal Stability of Type I and Type III Procollagen from Normal Human Fibroblasts and from a Patient with Osteogenesis Imperfecta", *PNAS USA* 77: 162–166 (1980).

Ala–Kokko et al., "Expression of Human Type II Procollagen Gene in Mouse Fibroblasts Transfected with a Chimeric Gene Construct Containing the Promoter of The Type I Procollagen Gene", J. Arth. Rheum. 37: S84 #75 (1989).

Vuorio, K. et al., "Characterization of the Human Prolyl 4–Hydroxylase Tetramer and its Multifunctional Protein Disulfide–Isomerase Subunit Synthesized in a Vaculovirus Expression System", PNAS USA 89: 7467–7470 (1992).

Helaakoski, T. et al., "Molecular Cloning of the α–Subunit of Human Prolyl 4–Hydroxylase: The Complete cDNA–Derived Amino Acid Sequence and Evidence for Alternative Splicing of RNA Transcripts", PNAS USA 86: 4392–4396 (1989).

Luckow, V. A. and Summers, "High Level Expression of Nonfused Foreign Genes with *Autographa californica* Nuclear Polyhedrosis Virus Expression Vectors", M.D. Virology 170: 31–39 (1989).

Pihlajaniemi T. et al., "Molecular Cloning of the β–Subunit of Human Prolyl 4–Hydroxylase. this Subunit and Protein Disulphide Isomerase are Products of the Same Gene", EMBO J. 6: 643–649 (1987).

Summers, M. D. and Smith, G. E., "A Manual of Methods for Baculovirus Vectors and insect Culture Procedures" Texas Agricultural Experiment Station Bull 1555: 1–56 by Texas A and M University, College Station, TX (1987).

Kivirikko, K. I. and Myllyla, R., "Posttranslational Enzymes in the Biosynthesis of Collagen: Intracellular Enzymes", Methods Enzymol. 82: 245–304 (1982).

Myllyla, R., Tuderman, L., and Kivirikko, K. I., "Mechanism of the Prolyl Hydroxylase Reaction 2. Kinetic Analysis of the Reaction Sequence", Eur. J. Biochem 80: 349–357 (1977).

Carmichael et al., "Purification and Characterization of a Thiol: Protein Disulfide Oxidoreductase from Bovine Liver", J. Biol. Chem. 252: 7163–7167 (1977).

Höyhtya M. et al., "Monoclonal Antibodies to Human Proly 4–Hydroxylase" Eur. J. Biochem 141: 477–482 (1984).

Kivirikko, K. I. and Myllyla, R., "Recent Developments in Posttranslational Modification: Intracellular Processing", Methods Enzymol. 144: 96–114 (1987).

Bassuk, et al., "Correlation of the steady–state RNA levels among the alpha–subunits of Prolyl 4–hydroxylase and the alpha–1 and alpha–2 chains of type I collagen during growth of chicken embryo tendon fibroblasts" *Biochem. Biophys. Res. Commun.*, 174(1):169–175, 1991.

Helaakoski, et al., "Increases in mRNA concentrations of the alpha and beta subunits of Prolyl 4–hydroylase accompany increased gene expression of type IV collagen during differentiation of mouse F9 cells" *J. Biol. Chem.*, 265(20): 11413–11416, 1990.

Wu, et al., "Human–mouse interspecies collagen I heterotrimer is functional during embryonic development of Mov13 mutant mouse embryos" *Mol. Cell. Beiol.*, 10(4): 1452–1460, 1990.

SYNTHESIS OF HUMAN PROCOLLAGENS AND COLLAGENS IN RECOMBINANT DNA SYSTEMS

GOVERNMENT RIGHTS

This invention was made in the course of research supported in part by NIH grants AR38188 and AR39740. The Government may have certain rights in this invention.

BACKGROUND OF THE INVENTION

This application is a continuation-in-part of U.S. application Ser. No. 08/037,728, filed as PCT/US92/09061 Oct. 27, 1992, now U.S. Pat. No. 5,405,757, which is a continuation of U.S. application Ser. No. 07/780,899, filed Oct. 23, 1991, now abandoned.

Expression of many exogenous genes is readily obtained in a variety of recombinant host-vector systems, but becomes difficult to obtain if the protein normally requires extensive post-translational processing. This is the likely reason that expression in a fully recombinant system has not been reported for any of the major fibrillar collagens that require processing by post-translational enzymes. See Prockop and Kivirikko, *N. Engl. J. Med.* 1984, 311, 376–386. Prolyl 4-hydroxylase is probably one of the most important post-translational enzyme necessary for synthesis of procollagen or collagen by cells because it is required to hydroxylate prolyl residues in the Y-position of the repeating -Gly-X-Y- sequences to 4-hydroxyproline. Prockop and Kivirikko, *N. Engl. J. Med.* 1984, 311,376–386. Unless an appropriate number of Y-position prolyl residues are hydroxylated to 4-hydroxyproline by prolyl 4-hydroxylase, the newly synthesize chains cannot fold into a triple-helical conformation at 37° C. If the hydroxylation does not occur, the polypeptides remain non-helical, are poorly secreted by cells, and cannot self-assemble into collagen fibrils. Recently, prolyl 4-hydroxylase, was expressed in baculovirus. Vuorio, K. et al., *Proceedings of the National Academy of Science, U.S.A.*, 1992, 89, 7467–7470.

Schnieke et al., *Proc. Natl. Acad Sci. U.S.A.* 1987, 84, 8869–8873 and Lee et al., *J. Biol. Chem.* 1989, 264, 20683–20687, disclose rescue experiments in two different systems that synthesized only one of the two chains for type I procollagen. Schnieke et al. reported that a gene for the human fibrillar collagen proα1(I) chain, the COL1A1 gene, can be expressed in mouse fibroblasts and that the chains are used to assemble molecules of type I procollagen, the precursor of type I collagen. However, in this system the proα2(I) chains found in the same molecule are of mouse origin. In the system of Lee et al. the proα1(I) chains are of rat origin. Thus, synthesis of a procollagen molecule in which all three chains are derived from an exogenous gene was not obtained by either Schnieke et al. or Lee et al.

Failure to obtain expression of genes for fibrillar collagens in a fully recombinant system has hampered attempts to study the normal structure-function relationships of the proteins and to study the effects of mutations. In particular, mutations in the gene for type II procollagen have recently been implicated as the cause of several human diseases, Anderson et al., *Am. J. Hum. Genet.* 1990, 46, 896–901; Tiller et al., *Proc. Natl. Acad. Sci. U.S.A.* 1990, 87, 3889–3893; Vissing et al., *J. Biol. Chem.* 1990, 264, 18265–18267; Lee et al., *Science* 1989, 244, 978–980; Francomano et al., *Genomics* 1987, 1, 293–296; Knowlton et al., *Am. J. Hum. Genet.* 1989, 45, 681–688; Ahmad et al., *Am. J. Hum. Genet.* 1990, 47, A206; Palotie et al., *The Lancet* 1989, I, 924–927; Knowlton et al., *N. Engl. J. Med.* 1990, 322, 526–530; Ala-Kokko et al., *Proc. Natl. Acad. Sci. U.S.A.* 1990, 87, 6565–6568, but because adequate numbers of human cartilage cells are difficult to obtain and because human chondrocytes readily lose their phenotype in culture, Elima and Vuorio, *FEBS Lett.* 1989, 258, 195–198; Aulthouse et al., *In Vitro Dev. Biol.* 1989, 25, 659–668, the causal relationship between a mutation in the gene and the biological function of the protein has proven elusive.

Also, failure to obtain expression of genes for human fibrillar collagens has made it impossible to prepare human fibrillar procollagens and collagens that have a number of therapeutic uses in man and that will not produce the undesirable immune responses that have been encountered with use of collagen from animal sources.

Recently however, Applicants described the expression of a human type II procollagen in mouse 3T3 cells using a promoter from the human type I procollagen gene. Ala-Kokko et al., *J. Biol. Chem.* 1991, 266, 14175; Ala-Kokko et al., *Matrix* 1990, 10, 234.

SUMMARY OF THE INVENTION

The present invention involves the preparation of gene constructs that contain collagen genes of human and other origins. One of the gene constructs is hybrid of a human gene for type I procollagen (COL1A1) and a human gene for type II procollagen (COL2A1). The 5'-end of the construct contains the promoter, exon 1 and intron 1 of the COL1A1 gene fused to intron 1 of the COL2A1 gene. The construct is designed so that the promoter and putative enhancer in the first intron of the COL1A1 drive expression of the COL2A1 gene and cause production of human type II procollagen. The COL2A1 gene consisted of two SphI/SphI fragments of the gene totalling about 26,000 base pairs. This construct contains all the coding sequences of the gene except for the few codons of a signal peptide in exon 1 and an alternatively spliced exon that follows exon 1. Some versions of the construct also include a 3,500 base pair SphI/SphI fragment from the 3'-end of the gene that is needed for correct polyadenylation of the mRNA.

A second construct has the promoter, the first exon, the intron, and about half of the second exon of the human COL1A1 gene as the 5'-fragment of the construct. The 5'-fragment is joined through a unique KpnI restriction endonuclease site to a cDNA that contains all the coding sequences of the gene except for those contained in the first one and one-half exons. In addition, the 3'-end of the cDNA is linked through an EcoRI site to an EcoRI/EcoRI fragment of about 0.5 kb from the 3'-end of the COL1A1 gene. A series of additional constructs use the highly active promoter for the cytomegalic virus to drive expression of full-length cDNA, for the human COL1A1 gene. All the constructs have been engineered so that they have unique restriction endonuclease sites at their 5'- and 3'-ends and, therefore, can be excised from vector sequences.

The present invention involves transfection and expression of collagen gene constructs into selected cells. In some preferred embodiments of the present invention, selected cells express one or more post-translational enzymes important to the biosynthesis of procollagens and collagens. For example, prolyl 4-hydroxylase is a post-translational enzyme important to the biosynthesis of procollagens and collagens. The enzyme must hydroxylate about 100 prolyl residues in the Y position of the repeating -Gly-X-Y tripeptide structures of procollagens and collagens to 4-hydroxyproline in order for the procollagens or collagens to fold into a stable triple-helical conformation at body temperature of the organism synthesizing the protein. Thus, in some preferred embodiments of the present invention cells which express prolyl 4-hydroxylase are preferred. Such cells may naturally express the post-translational enzymes, or may be transformed with genes coding for post-translational enzymes such as prolyl 4-hydroxylase. Mammalian cells, insect cells, or yeast cells are preferred. Mammalian cells, insect cells and yeast cells which are transfected with at least one set of genes coding for a post-translational enzyme such as prolyl 4-hydroxylase, may also be transfected with collagen gene constructs in yet other preferred embodiments of the present invention. The invention can also employ other cells that can be cultured and contain the necessary post translational enzymes and secretory mechanisms, such as chinese hamster ovary cells.

DETAILED DESCRIPTION OF THE INVENTION

It has been established that most forms of osteogenesis imperfecta (OI) are caused by dominant mutations in one of the two genes for type I procollagen. Also, at least a subset of post-menopausal osteoporosis is caused by similar mutations in the two genes for type I procollagen. It has further been reported that mutations in the type II procollagen gene cause human diseases such as chondrodysplasia, and a subset of primary generalized osteoarthritis. It has further been reported that mutations in the type III procollagen gene (COL3A1) cause human diseases such as a lethal variant of Ehlers-Danlos syndrome (type IV) and familial aneurysms. Moreover, it has been demonstrated that the kidney disease known as the Alport syndrome is caused by mutations in one of the genes (COL4A5) for type IV collagen. It has further been demonstrated that injections of suspensions of collagen fibers are effective for the treatment of cosmetic defects as well as physical weakness of tissues such as sphincters.

The present invention concerns cells in which one of these fibrillar procollagens is expressed both as mRNA and as a protein. Additionally, the present invention concerns types I, II, and III procollagens expressed in a mammalian cell line, an insect cell line, or a yeast cell line, and the establishment of transfected cell lines comprising these procollagen genes.

The present invention further provides that the gene constructs can be used to synthesize human fibrillar procollagens in the HT-1080 human tumor cell line. This human cell line has been a ready source of type IV collagen, the major collagen of basement membranes. Because type IV collagen is not a fibril-forming procollagen or collagen, it can be readily separated by a simple chromatographic procedure from any fibrillar procollagen. Hence, the invention provides methods whereby a human fibrillar procollagen can be readily separated from products of an endogenous collagen gene. Moreover, HT-1080 cells grow extremely rapidly in culture and can be maintained for long periods of time.

Figure 4:
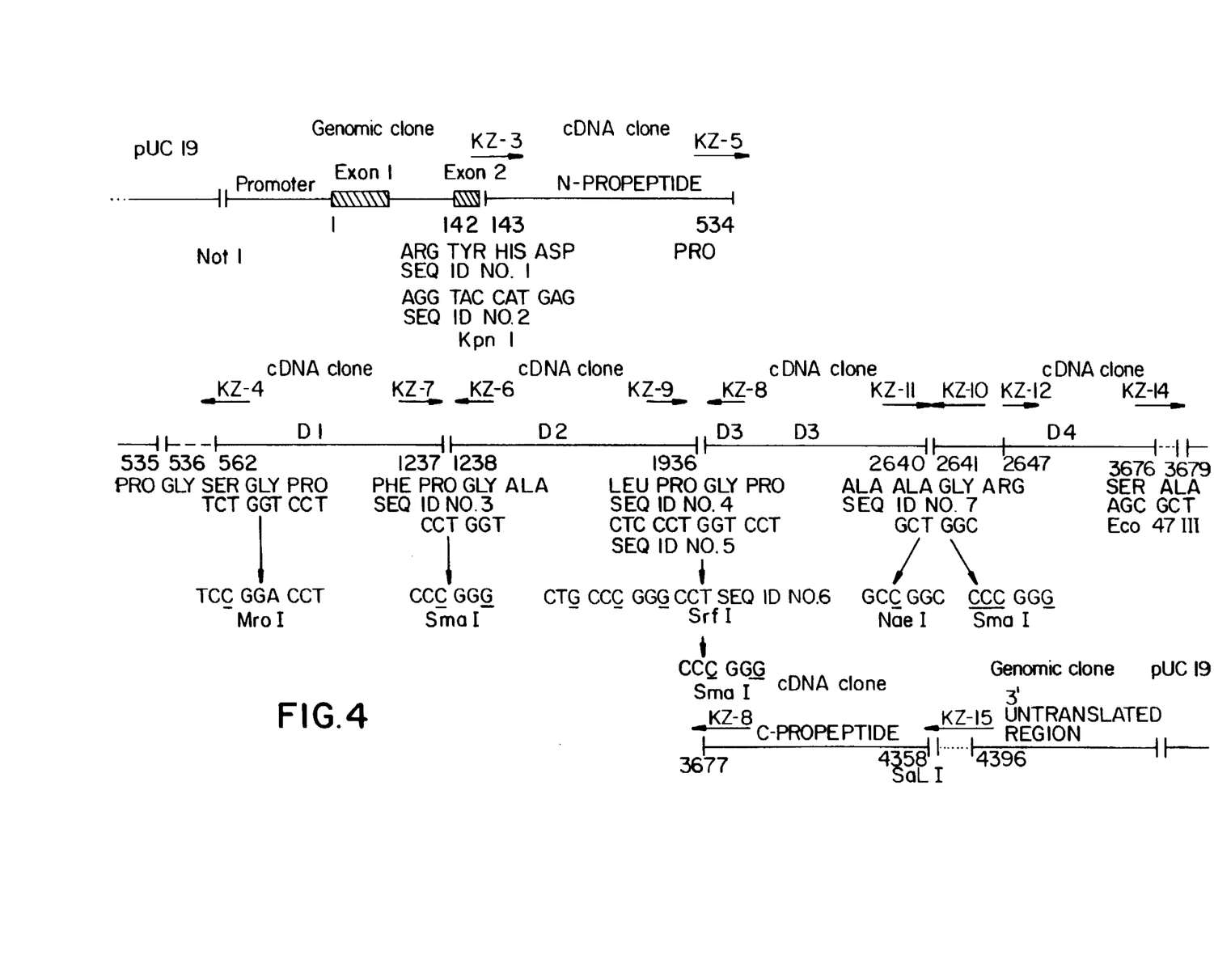
FIG. 4 is a schematic representation of the cDNA for the proα1(I) chain of human type I procollagen that has been modified to contain artificial sites for cleavage by specific restriction endonucleases.

Additionally, the present invention provides for a single procollagen or collagen gene or a number of different procollagen or collagen genes expressed within a cell. Further, it is contemplated that the there can be a one or more copies of a single procollagen or collagen gene or of the number of different such genes transfected into cells and expressed. The present invention provides that these cells can be transfected so that- they express at least one human procollagen gene, especially but not limited to the COL1A1 gene encoding the proα1(I) procollagen chain of human type I procollagen. It is also provided that the cells can be transfected with and express both COL1A1 and COL1A2 genes so that both proα2(I) and proα1(I) chains are simultaneously synthesized and assembled into normal heterotrimeric molecules of type I procollagen. Moreover, the present invention provides that cells can be transfected with and express the COL2A1 gene encoding the proα1(II) chain of human type II procollagen. It is further provided that cells can be transfected with and express the COL3A1 gene encoding the proα1(III) chain of type III procollagen. The invention also provides that any procollagen or collagen gene transfected into and expressed within cells may comprise a mutant, variant, hybrid or recombinant gene. Such mutant, variant, hybrid or recombinant gene may include a mutation which provides unique restriction sites for cleavage of the hybrid gene. In some preferred embodiments of the present invention, mutations providing one or more unique restriction sites do not alter the amino acid sequence encoded by the gene, but merely provide unique restriction sites useful for manipulation of the gene. Thus, the modified gene would be made up of a number of discrete regions, or D-regions, flanked by unique restriction sites. These discrete regions of the gene are herein referred to as cassettes. For example, cassettes designated as D1 through D4.4 are shown in FIG. 4. Multiple copies of a gene cassette is another variant of the present gene which is encompassed by the present invention. Recombinant or mutant genes or cassettes which provide desired characteristics such as resistance to endogenous enzymes such as collagenase are also encompassed by the present invention. Further, the present invention provides transfected cells substantially all of which comprise other procollagen or collagen genes, preferably but not limited to types I, II, III procollagen genes or type IV collagen genes. The present invention contemplates that transfected cells may be mammalian cells such as human tumor cells, especially but not limited to HT-1080 cells. In other embodiments of the present invention, transfected cells are insect cells such as baculovirus Sf9 cells. In still other embodiments of the present invention, transfected cells are yeast cells, such as *Saccharomyces cerevisiae* or *Pichia pastoris* cells. In preferred embodiments of the present invention, cells such as mammalian, insect and yeast cells, which may not naturally produce sufficient amounts of post translational enzymes, are transformed with at least one set of genes coding for a post-translational enzyme such as prolyl 4-hydroxylase.

The present invention further contemplates cells substantially all of which comprise at least one transfected human procollagen or collagen gene having at least one chain derived from a transfected or collagen procollagen gene or genes and at least one chain derived from an endogenous human or non-human procollagen gene or genes, other than the [proα1(I)]$_2$proα2(I) collagen molecule consisting of human proα1(I) moieties and non-human proα2(I) moieties, or non-human proα1(I) moieties and human proα2(I) moieties.

A novel feature of the methods of the invention is that relatively large amounts of a human fibrillar procollagen can be synthesized in a recombinant cell culture system that does not make any other fibrillar procollagen. Systems that make other fibrillar procollagens or collagens are impractical because of the extreme difficulty of purifying the product of the endogenous genes for fibrillar procollagen or collagen from products of the recombinant genes. Using methods of the present invention, purification of human procollagen is greatly facilitated. Moreover, it has been demonstrated that the amounts of protein synthesized by the methods of the present invention are high relative to other systems used in the art.

Other novel features of the methods of present invention are that procollagens synthesized are correctly folded proteins so that they exhibit the normal triple-helical conformation characteristic of procollagens and collagens. Therefore, the procollagens can be used to generate stable collagen fibrils and fibers by cleavage of the procollagens with proteases.

The present invention is in contrast to Schnieke et al., who reported that a gene for the human fibrillar procollagen proα1(I) chain, the COL1A1 gene, can be expressed in mouse fibroblasts and the chains used to assemble molecules of type I procollagen, the precursor of type I collagen. However, in the system of Schnieke et al., the proα2(I) chains found in the molecule of type I procollagen were of mouse origin. Hence, the type I procollagen synthesized is a hybrid molecule of human and mouse origin. Similarly, the system of Lee et al. expressed an exogenous proα2(I) gene to generate type I procollagen in which the proα1(I) chains were of rat origin. The present invention provides methods for the production of procollagens or collagens derived solely from transfected procollagen and collagen genes, but these methods are not limited to the production of procollagen and collagen derived solely from transfected genes.

An advantage of human collagens of the present invention is that these collagens will not produce allergic responses in man. Moreover, collagen of the present invention prepared from cultured cells should be of a higher quality than collagen obtained from animal sources, and should form larger and more tightly packed fibers. These higher quality proteins should form deposits in tissues that last much longer than the currently available commercial materials. It is known that using currently available methods, most injections of collagen for cosmetic purposes have to be repeated as frequently as every 6 months. Human protein of the present invention should last much longer after injection into human tissues.

Methods of the present invention provide a practical source of a human fibrillar collagen similar to animal collagens that are widely used for injection to remove cosmetic wrinkles, and cosmetic defects of other natures, and are also being used to restore the tensile strength of tissues such as the sphincter of the bladder in the treatment of urinary incontinence. Animal collagens are also used in mixtures with ceramics and other materials to fill in defects in bone and enhance bone growth. Type I collagen from animal sources has been used commercially. However, a convenient source of human collagen for therapeutic use is still sorely needed.

Further, the present invention contemplates that human type II procollagen, the precursor of the major collagen of cartilage may have special use in the repair of cartilage damage. Moreover, modified human type I procollagen comprising a proα1(I) trimer expressed according to the methods in the present invention is also contemplated. Also, type I procollagen comprised of two proα1(I) and one proα2(I) chains derived from transfected human genes is contemplated. Also, type III procollagen comprised of three proα1(III) chains derived from transfected human genes is contemplated. In addition, specifically engineered forms of these collagens are contemplated.

Methods are provided for synthesizing fibrillar collagen in cells comprising transfecting at least one human procollagen or collagen gene into cells and selecting transfected cells that comprise molecules derived from a procollagen or collagen gene or genes, other than the [proα1(I)]$_2$proα2(I) molecule consisting of human proα1(I) moieties and non-human proα2(I) moieties, or non-human α1(I) moieties and human α2(I) moieties. Further, methods whereby at least one of the human procollagen genes is a mutant, variant, hybrid or recombinant gene are also contemplated. Additionally, the present invention provides methods whereby substantially all cells transfected with at least one procollagen gene comprise type III and other procollagen genes. Further, methods are contemplated wherein transfected cells are human tumor cells, especially but not limited to HT-1080 cells. Methods are also provided whereby transfected cells comprise independently substantially no endogenously derived collagen molecules, endogenously derived type I procollagen molecules, endogenously derived type II procollagen molecules, endogenously derived type III procollagen molecules, or endogenously derived type IV collagen molecules. Other methods are provided whereby substantially all of the transfected cells comprise at least one transfected human procollagen gene and express procollagen or collagen molecules having at least one chain derived from the transfected gene, other than the [proα1(I)]$_2$proα2(I) collagen consisting of human proα1(I) moieties and non-human proα2(I) moieties, or non-human proα1(I) moieties and human proα2(I) moieties. Other preferred methods are provided whereby substantially all transfected cells comprise at least one transfected human procollagen gene and express procollagen molecules having three chains derived from the transfected collagen gene or genes.

The present invention is further illustrated by the following examples, which are not intended to be limiting in any way.

EXAMPLES

EXAMPLE 1

Synthesis of Human Type II Procollagen

A recombinant COL1A1 gene construct employed in the present invention comprised a fragment of the 5'-end of COL1A1 having a promotor, exon 1 and intron 1 fused to exons 3 through 54 of a COL2A1 gene. The hybrid construct was transfected into HT-1080 cells. These cells were co-transfected with a neomycin-resistance gene and grown in the presence of the neomycin analog G418. The hybrid construct was used to generate transfected cells.

Figure 1:
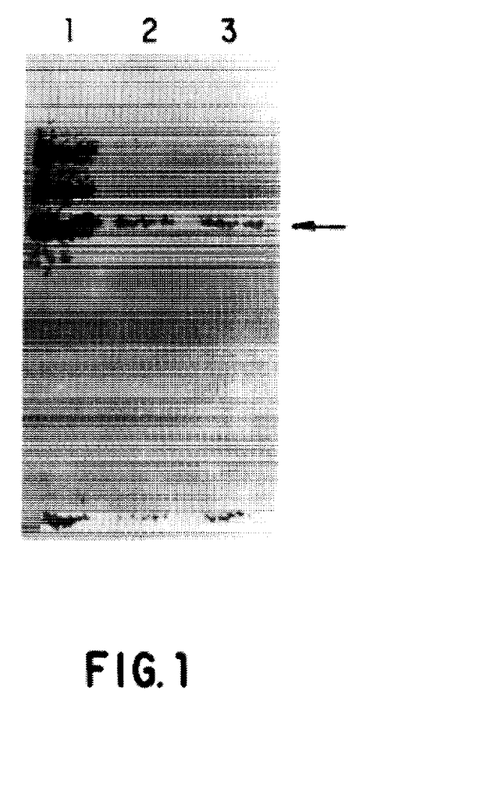
FIG. 1 is a photograph showing analysis by polyacrylamide gel electrophoresis in SDS of the proteins secreted into medium by HT-1080 cells that were transfected with a gene construct containing the promoter, first exon and most of the first intron of the human COL1A1 gene linked to 30 kb fragment containing all of COL2A1 except the first two exons. The cells were incubated with [$^{14}$C]proline so that the medium proteins could be analyzed by autoradiography (storage phosphor film analyzer). Lane 1 shows that the unpurified medium proteins are comprised of three major polypeptide chains. The upper two are proα1(IV) and proα2(IV) chains of type IV collagen that are synthesized by cells not transfected by the construct (not shown). The third band is the proα1(II) chains of human type II procollagen synthesized from the construct. Lanes 2 and 3 are the same medium protein after chromatography of the medium on an ion exchange column (DE-52, Whatman, at pH 7.4 in lane 2 and at pH 7.0 in lane 3). The type II procollagen appeared in the void volume of the ion exchange column.
Figure 2:
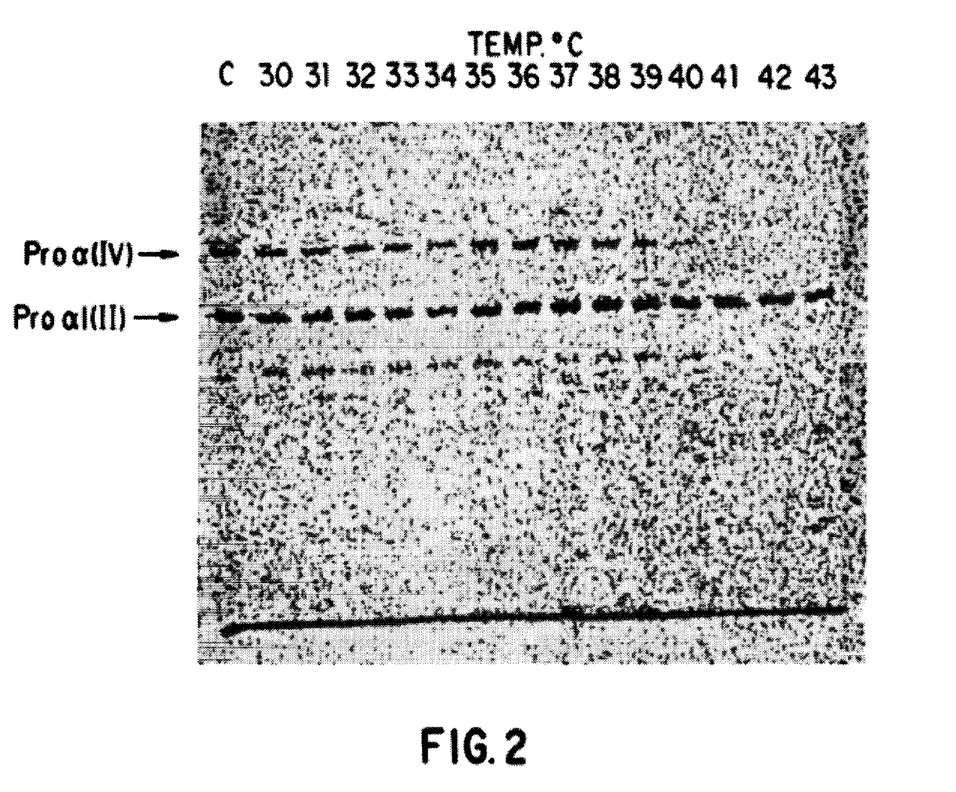
FIG. 2 is a photograph showing that the type II procollagen secreted into the medium from cells described in FIG. 1 was folded into a correct native conformation. The medium proteins were digested at the temperatures indicated with a high concentration of trypsin and chymotrypsin under conditions in which correctly folded triple-helical procollagen or collagen resists digestion but unfolded or incorrectly folded procollagen of collagen is digested to small fragments (Bruckner and Prockop, *Anal. Biochemistry* 1981, 110, 360). The products of the digestion were then analyzed by polyacrylamide gel electrophoresis in SDS and fluorography. The results show that the type II procollagen resisted digestion up to 43° C., the normal temperature at which type II procollagen unfolds. Therefore, the type II procollagen is correctly folded and can be used to generate collagen fibrils.

A series of clones were obtained that synthesized mRNA for human type II procollagen. To analyze the synthesized proteins, the cells were incubated with [$^{14}$C]proline and the $^{14}$C-labeled medium proteins were analyzed by gel electrophoresis. See FIG. 1. As indicated in Lane 1, the medium proteins contained the expected type II procollagen comprised of proα1(II) chains together with prowl(IV) and proα2(IV) chains of type IV collagen normally synthesized by the cells. As indicated in Lanes 2 and 3, the type II procollagen was readily purified by a single step of ion exchange chromatography. The type II procollagen secreted into the medium was correctly folded by a protease-thermal stability test. See FIG. 2.

EXAMPLE 2

Synthesis of Human Type I Procollagen

Figure 3:
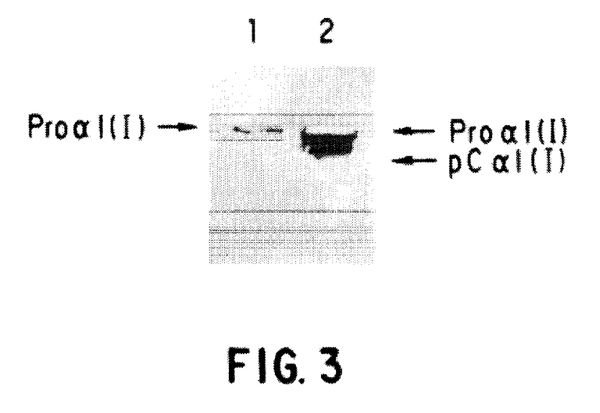
FIG. 3 is a photograph showing analysis of medium of HT-1080 cells co-transfected with a gene for COL1A1 and a gene for COL1A2. THE COL1A2 was linked to an active neomycin-resistance gene but the COL1A1 was not. The cells were screened for expression of the COL1A2-neomycin resistance gene construct with the neomycin analog G418. The medium was analyzed for expression of the COL1A1 by Western blotting with a polyclonal antibody specific for the human proα1(I) chain. Lane 1 indicates that the medium proteins contained proα(I) chains. Lane 2 is an authentic standard of type I procollagen containing proα1(I) chains and partially processed pCα1(I) chains. The results demonstrate that the cells synthesized human type procollagen that contained proα1(I) chains, presumably in the form of the normal heterotrimer with the composition two proα(I) chains and one proα2(I) chain.

As a second example, HT-1080 cells were co-transfected with a COL1A1 gene and a COL1A2 gene. Both genes consisted of a cytomegalic virus promoter linked to a full-length cDNA. The COL1A2 gene construct but not the COL1A1 gene construct contained a neomycin-resistance gene. The cells were selected for expression of the COL1A2-neomycin resistance gene construct by growth in the presence of the neomycin-analog G418. The medium was then examined for expression of the COL1A1 with a specific polyclonal antibody for human proα1(I) chains. The results (see FIG. 3) demonstrated that the cells synthesized human type I procollagen that was probably comprised of the normal heterotrimeric structure of two proα1(I) chains and one proα2(I) chain.

Table 1 presents a summary of the DNA constructs containing human procollagen genes. The constructs were assembled from discrete fragments of the genes or cDNAs from the genes together with appropriate promoter fragments.

TABLE 1

| Constructs | 5'-end | Central Region | 3'-end | Protein product |
|---|---|---|---|---|
| A | Promoter (2.5 kb) + exon 1 + intron 1 from COL1A1 | Exons 3 to 54 from COL2A1 | 3.5 kb SphI/SphI fragment from 3'-end of COL2A1 | Human type II procollagen, [proα1(II)]$_3$ |
| B | Promoter (2.5 kb) of COL1A1 | Exons 1 to 54 from COL2A1 | 3.5 kb SphI/SphI fragment from 3'-end of COL2A1 | Human type II procollagen, [proα1(II)]$_3$ |
| C | Promoter (2.5 kb) + exon 1 + intron 1 + half of exon 2 from COL1A1 | cDNA for COL1A1 except for first 1½ exons | 0.5 kb fragment from COL1A1 | Human type I procollagen, [proα1(I)]$_3$ |
| D | Cytomegalic virus promoter | cDNA from COL1A1 | | Human type I procollagen, [proα1(I)]$_3$ |
| E | Cytomegalic virus promoter | cDNA from COL1A2 | | Human type I [proα1(I)]$_2$proα2(I)] when expressed with construct C or D |

EXAMPLE 3

Cell Transfections

For cell transfection experiments, a cosmid plasmid clone containing the gene construct was cleaved with a restriction endonuclease to release the construct from the vector. A plasmid vector comprising a neomycin resistance gene, Law et al., *Molec. Cell Biol.* 1983, 3, 2110–2115, was linearized by cleavage with BamHI. The two samples were mixed in a ratio of approximately 10:1 gene construct to neomycin-resistant gene, and the mixture was then used for co-transfection of HT-1080 cells by calcium phosphate co-precipitation, Sambrook et al., *Molecular Cloning, A Laboratory Manual*, Cold Spring Harbor Laboratory Press, Second Edition (1989). DNA in the calcium phosphate solution was layered onto cultured cells with about 10 μg of chimeric gene construct per 100 ml plate of preconfluent cells. Cells were incubated in DMEM containing 10% newborn calf serum for 10 hours. The samples were subjected to glycerol shock by adding a 15% glycerol solution for 3 minutes. The cells were then transferred to DMEM medium containing newborn calf serum for 24 hours and then to the same medium containing 450 μg/ml of G418. Incubation in the medium containing G418 was continued for about 4 weeks with a change of medium every third day. G418-resistant cells were either pooled or separate clones obtained by isolating loci with a plastic cylinder and subcultured.

EXAMPLE 4

Western blotting

For assay of expression of the COL2A1 gene, polyclonal antibodies were prepared in rabbits using a 23-residue synthetic peptide that had an amino acid sequence found in the COOH-terminal telopeptide of type II collagen. See Cheah et al., *Proc. Natl. Acad. Sci. U.S.A.* 1985, 82, 2555–2559. The antibody did not react by Western blot analysis with proα chains of human type I procollagen or collagen, human type II procollagen or collagen, or murine type I procollagen. For assay of expression of the COL1A1 genes, polyclonal antibodies that reacted with the COOH-terminal polypeptide of the proα1(I) chain were employed. See Olsen et al., *J. Biol. Chem.* 1991, 266, 1117–1121.

Culture medium from pooled clones or individual clones was removed and separately precipitated by the addition of solid ammonium sulfate to 30% saturation and precipitates were collected by centrifugation at 14,000 x g and then dialyzed against a buffer containing 0.15M NaCl, 0.5mM EDTA, 0.5 mM N-ethylmaleimide, 0.1 mM and p-aminobenzamidine, and 50mM Tris-HCl (pH 7.4 at 4° C.). Aliquots of the samples were heated to 10° C. for 5 minutes in 1% SDS, 50 mM DTT and 10% (v/v) glycerol, and separated by electrophoresis on 6% polyacrylamide gels using a mini-gel apparatus (Holford SE250, Holford Scientific) run at 125 V for 90 minutes. Separated proteins were electroblotted from the polyacrylamide gel at 40 V for 90 minutes onto a supported nitrocellulose membrane (Schleicher and Schuell). The transferred proteins were reacted for 30 minutes with the polyclonal antibodies at a 1:500 (v/v) dilution. Proteins reacting with the antibodies were detected with a secondary anti-rabbit IgG antibody coupled to alkaline phosphatase (Promega Biotech) for 30 minutes. Alkaline phosphatase was visualized with NBT/BCIP (Promega Biotech) as directed by the manufacturer.

EXAMPLE 5

Demonstration of Correct Folding of the Secreted Procollagens

To demonstrate that the procollagens synthesized and secreted in the medium by the transfected cells were correctly folded, the medium proteins were digested with high concentrations of proteases under conditions in which only correctly folded procollagens and collagens resist digestion. For digestion with a combination of trypsin and chymotrypsin, the cell layer from a 25 cm flask was scraped into 0.5 ml of modified Krebs II medium containing 10 mM EDTA and 0.1% Nonidet P-40 (Sigma). The cells were vigorously agitated in a Vortex mixer for 1 minute and immediately cooled to 4° C. The supernatant was transferred to new tubes. The sample was preincubated at the temperature indicated for 10 minutes and the digestion was carried out at the same temperature for 2 minutes. For the digestion, a 0.1 volume of the modified Krebs II medium containing 1 mg/ml trypsin and 2.5 mg/ml α-chymotrypsin (Boehringer Mannheim) was added. The digestion was stopped by adding a 0.1 volume of 5 mg/ml soybean trypsin inhibitor (Sigma).

For analysis of the digestion products, the sample was rapidly immersed in boiling water for 2 minutes with the concomitant addition of a 0.2 volume of 5 x electrophoresis sample buffer that consisted of 10% SDS, 50% glycerol, and 0.012% bromphenol blue in 0.625M Tris-HCl buffer (pH 6.8). Samples were applied to SDS gels with prior reduction by incubating for 3 minutes in boiling water after the addition of 2% 2-mercaptoethanol. Electrophoresis was performed using the discontinuous system of Laemmli, *Nature* 1979, 227, 680–685, with minor modifications described by de Wet et al., *Journal of Biological Chemistry* 1983, 258, 7721–7728.

EXAMPLE 6

Specifically Engineered Procollagens and Collagens

As indicated in FIG. 4, a hybrid gene consisting of some genomic DNA and some cDNA for the proα(I) chain of human type I procollagen was the starting material. The DNA sequence of the hybrid gene was analyzed and the codons for amino acids that formed the junctions between the repeating D-periods were modified in ways that did not change the amino acids encoded but did create unique sites for cleavage of the hybrid gene by restriction endonucleases.

A. Recombinant procollagen or collagen

The D3-period of proα1(I) is excised using SrfI and NaeI restriction nucleases. The bases coding for the amino acids found in the collagenase recognition site present in the D3 period are modified so that they code for a different amino acid sequence. The cassette is amplified and reinserted in the gene. Expression of the gene in an appropriate host cell will result in type I collagen which can not be cleaved by collagenase.

B. Procollagen or collagen deletion mutants

A D2 period cassette (of the proα1(I) chain) is excised from the gene described above by digestion with SmaI. The gene is reassembled to provide a gene having a specific in-frame deletion of the codons for the D2 period.

C. Procollagen or collagen addition mutants

Multiple copies of one or more D-cassettes may be inserted at the engineered sites to provide multiple copies of desired regions of procollagen or collagen.

EXAMPLE 7

Expression of Human Prolyl 4-Hydroxylase in a Recombinant DNA System

To obtain expression of the two genes for prolyl 4-hydroxylase in insect cells, the following procedures were carried out. The baculovirus transfer vector pVLα58 was constructed by digesting a pBluescript (Stratagene) vector containing in the SmaI site the full-length cDNA for the α subunit of human prolyl 4-hydroxylase, PA-58 (Helaakoski, T. et al., *Proc. Natl. Acad. Sci. U.S.A.* 1989, 86, 4392–4396), with PstI and BamHI, the cleavage sites which closely flank the SmaI site. The resulting PstI-PstI and PstI-BamHI fragments containing 61 bp of the 5' untranslated sequence, the whole coding region, and 551 bp of the 3' untranslated sequence were cloned to the PstI-BamHI site for the baculovirus transfer vector pVL1392 (Luckow, V. A. and Summers, M. D., *Virology* 1989, 170, 31–39). The baculovirus transfer vector pVLα59 was similarly constructed from pVL1392 and another cDNA clone, PA-59 (Helaakoski, T. et al., supra), encoding the α subunit of human prolyl 4-hydroxylase. The cDNA clones PA-58 and PA-59 differ by a stretch of 64 bp.

The pVLβ vector was constructed by ligation of an EcoRI-BamHI fragment of a full-length cDNA for the β subunit of human prolyl 4-hydroxylase, S-138 (Pihlajaniemi, T. et al., *EMBO J.* 1987, 6, 643–649) containing 44 bp of the 5' untranslated sequence, the whole coding region, and 207 bp of the 3' untranslated sequence to EcoRI/BamHI-digested pVL1392. Recombinant baculovirus transfer vectors were cotransfected into Sf9 cells (Summers, M. D. and Smith, G. E., *Tex. Agric. Exp. St. Bull.* 1987, 1555, 1–56) with wild-type Autographa californica nuclear polyhedrosis virus (AcNPV) DNA by calcium phosphate transfection. The resultant viral pool in the supernatant of the transfected cells was collected 4 days later and used for plaque assay. Recombinant occlusion-negative plaques were subjected to three rounds of plaque purification to generate recombinant viruses totally free of contaminating wild-type virus. The screening procedure and isolation of the recombinant viruses essentially followed by the method of Summers and Smith, supra. The resulting recombinant viruses from pVLα58, pVLα59, and pvLβ were designated as the α58 virus, α59 virus and β virus, respectively.

Sf9 cells were cultured in TNM-FH medium (Sigma) supplemented with 10% fetal bovine serum at 27° C. either as monolayers or in suspension in spinner flasks (Techne). To produce recombinant proteins, Sf9 cells seeded at a density of $10^6$ cells per ml were injected at a multiplicity of 5–10 with recombinant viruses when the α58, α59, or β virus was used alone. The α and β viruses were used for infection in ratios of 1:10–10:1 when producing the prolyl 4-hydroxylase tetramer. The cells were harvested 72 hours after infection, homogenized in 0.01M Tris, pH 7.8/0.1 M NaCl/0.1M glycine/10 µM dithiothreitol/0.1% Triton X-100, and centrifuged. The resulting supernatants were analyzed by SDS/10% PAGE or nondenaturing 7.5% PAGE and assayed for enzyme activities. The cell pellets were further solubilized in 1% SDS and analyzed by SDS/10% PAGE. The cell medium at 24–96 hours postinfection was also analyzed by SDS/10% PAGE to identify any secretion of the resultant proteins into the medium. The cells in these experiments were grown in TNM-FH medium without serum.

When the time course of protein expression was examined, Sf9 cells infected with recombinant viruses were labeled with [$^{35}$S]methionine (10 µCi/µl; Amersham; 1 Ci=37 CBq) for 2 hours at various time points between 24 and 50 hours after infection and collected for analysis by SDS/10% PAGE. To determine the maximal accumulation of recombinant protein, cells were harvested at various times from 24 to 96 hours after infection and analyzed on by SDS/10% PAGE. Both the 0.1% Triton X-100- and 1% SDS-soluble fractions of the cells were analyzed. Prolyl 4-hydroxylase activity was assayed by a method based on the decarboxylation of 2-oxo[1-$^{14}$C]glutarate (Kivirikko, K. I., and Myllyla, R., *Methods Enzymol.* 1982, 82, 245–304). The Km values were determined by varying the concentrations of one substrate in the presence of fixed concentration of the second, while the concentrations of the other substrates were held constant (Myllyla, R., Tuderman, L., and Kivirikko, K. I., *Eur. J. Biochem.* 1977, 80, 349–357). Protein disulfide-isomerase activity of the β subunit was measured by glutathione:insulin transhydrogenase assay (Carmichael et al., *J. Biol. Chem.* 1977, 252, 7163–7167). Western blot analysis was performed using a monoclonal antibody, 5B5, to the β subunit of human prolyl 4-hydroxylase (Hoyhtya, M. et al., *Eur. J. Biochem.* 1984, 141, 477–482). Prolyl 4-hydroxylase was purified by a procedure consisting of poly(L-proline) affinity chromatography, DEAE-cellulose chromatography, and gel filtration (Kivirikko, K. I., and Myllyla, R., *Methods Enzymol.* 1987, 144, 96–114).

Figure 5:
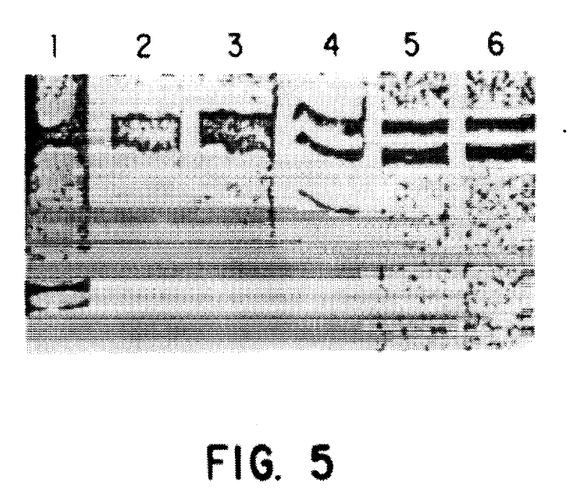
FIG. 5 is a photograph showing analysis by non-denaturing 7.5% polyacrylamide gel electrophoresis (lanes 1–3) and 10% polyacrylamide gel electrophoresis in SDS (lanes 4–6) of purified chick prolyl 4-hydroxylase (lanes 1 and 4) and the proteins secreted into medium by Sf9 cells expressing the gene for the α-subunit and the β-subunit of human prolyl 4-hydroxylase and infected with α58/β virus (lanes 2 and 5) or with α59/β virus (lanes 3 and 6). α58/β and α59/β differ by a stretch of 64 base pairs. Lanes 1–3 are protein separated under non-denaturing conditions and showing tetramers of the two kinds of subunits. Lanes 4–6 are the same samples separated under denaturing conditions so that the two subunits appear as separate bands.

FIG. 5 presents analysis of the prolyl 4-hydroxylase synthesized by the insect cells after purification of the protein by affinity-column chromatography. When examined by polyacrylamide gel electrophoresis in a non-denaturing gel, the recombinant enzyme co-migrated with the tetrameric and active form of the normal enzyme purified from chick embryos. After the purified recombinant enzyme was reduced, the α- and β- subunits were detected. Table 2 presented data on the enzymic activity of the recombinant enzyme. The Km values were determined by varying the concentration of one substrate in the presence of fixed concentrations of the second while the concentration of the other substrates were held constant.

TABLE 2

| Substrate | Km value, µM | | |
|---|---|---|---|
| | $\alpha58_2\beta_2$ | $\alpha59_2\beta_2$ | Chick enzyme |
| $Fe^{+2}$ | 4 | 4 | 4 |
| 2-oxoglutarate | 22 | 25 | 22 |
| ascorbate | 330 | 330 | 300 |
| (Pro—Pro—Gly)$_{10}$ | 18 | 18 | 15–20 |

As indicated, the Michales-Menton (Km) values for the recombinant enzyme were the same as for the authentic normal enzyme from chick embryos.

Since the transfected insect cells synthesize large amounts of active prolyl 4-hydroxylase, they are appropriate cells to transfect with genes of the present invention coding for procollagens and collagens so as to obtain synthesis of large amounts of the procollagens and collagens. Transfection of the cells with genes of the present invention is performed as described in Example 3.

EXAMPLE 8

Expression of Recombinant Collagen Genes in *Sacchharomyces cerevisiae* Yeast Expressing Recombinant Genes for Prolyl 4-Hydroxylase The yeast *Saccharomyces cerevisiae* can be used with any of a large number of expression vectors. One of the most commonly employed expression vectors is the multi-copy 2 µ plasmid that contains sequences for propagation both in yeast and *E. coli*, a yeast promoter and terminator for efficient transmission of the foreign gene. Typical examples of such vectors based on 2 µ plasmids are pWYG4 that has the 2 µ ORISTB elements, the GAL1 promoter, and the 2 µ D gene terminator. In this vector an NcoI cloning site containing the ATG that is used to insert the gene for either the α or β subunit of prolyl 4-hydroxylase. As another example, the expression vector can be pWYG7L that has intact 2 µ ORI, STB, REP1 and REP2, the GAL7 promoter, and uses the FLP terminator. In this vector, the gene for either the α or β subunit of prolyl 4-hydroxylase is inserted in the polylinker with its 5' ends at a BamHI or NcoI site. The vector containing the prolyl 4-hydroxylase gene is transformed into *S. cerevisiae* either after removal of the cell wall to produce spheroplasts that take up DNA on treatment with calcium and polyethylene glycol or by treatment of intact cells with lithium ions. Alternatively, DNA can be introduced by electroporation. Transformants can be selected by using host yeast cells that are auxotrophic for leucine, tryptophane, uracil or histidine together with selectable marker genes such as LEU2, TRP1, URA3, HIS3 or LEU2-D. Expression of the prolyl 4-hydroxylase genes driven by the galactose promoters can be induced by growing the culture on a non-repressing, non-inducing sugar so that very rapid induction follows addition of galactose; by growing the culture in glucose medium and then removing the glucose by centrifugation and washing the cells before resuspension in galactose medium; and by growing the cells in medium containing both glucose and galactose so that the glucose is preferentially metabolized before galactose-induction can occur. Further manipulations of the transformed cells are performed as described above to incorporate genes for both subunits of prolyl 4-hydroxylase and desired collagen or procollagen genes into the cells to achieve expression of collagen and procollagen that is adequately hydroxylated by prolyl 4-hydroxylase to fold into a stable triple helical conformation and therefore accompanied by the requisite folding associated with normal biological function.

EXAMPLE 9

Expression of Recombinant Collagen Genes in *Pichia pastoris* Yeast Expressing Recombinant Genes for Prolyl 4-Hydroxylase Expression of the genes for prolyl 4-hydroxylase and procollagens or collagens can also be in non-Saccharomyces yeast such as *Pichia pastoris* that appear to have special advantages in producing high yields of recombinant protein in scaled-up procedures. Typical expression in the methylotroph *P. pastoris* is obtained by the promoter from the tightly regulated AOX1 gene that encodes for alcohol oxidase and can be induced to give high levels of recombinant protein driven by the promoter after addition of methanol to the cultures. Since *P. Pastoris* has no native plasmids, the yeast is employed with expression vectors designed for chromosomal integration and genes such as HIS4 are used for selection. By subsequent manipulations of the same cells expression of genes for procollagens and collagens described herein is achieved under conditions where the recombinant protein is adequately hydroxylated by prolyl 4-hydroxylase and, therefore, can fold into a stable helix that is required for the normal biological function of the proteins in forming fibrils.

What is claimed:

1. Recombinant eukaryotic host cells comprising at least one transfected human procollagen or collagen gene, wherein said transfected human collagen or procollagen gene is selected from the group consisting of a gene encoding at least one polypeptide chain of human type I, human type II, or human type III procollagen or collagen, and at least one transfected gene encoding prolyl 4-hydroxylase or a subunit of prolyl 4-hydroxylase.

2. The cells of claim 1 wherein said transfected collagen or procollagen gene is selected from the group consisting of COL1A1, COL1A2, COL2A1, and COL3A1.

3. The cells of claim 1 wherein one of said transfected human procollagen gene is the COL1A1 gene encoding the proα1(I) chain of human type I procollagen.

4. The cells of claim 3 further comprising a transfected procollagen gene is the COL1A2 gene encoding the proα2(I) chain of human type I procollagen.

5. The cells of claim 1 wherein one of said transfected human procollagen gene is the COL2A1 gene encoding the proα1(II) chain of human type II procollagen.

6. The cells of claim 1 wherein one of said transfected human procollagen gene is the COL3A1 genes encoding the proα1(III) chain of the human type III procollagen.

7. The cells of claim 1 wherein said collagen or procollagen comprises at least one collagenase recognition site.

8. The cells of claim 1 wherein said host cells are non-human mammalian cells.

9. The cells of claim 1 wherein said host cells are insect cells.

10. The cells of claim 1 wherein said host cells are yeast cells.

11. The yeast cells of claim 10 wherein said cells are *Saccharomyces cervisiae*.

12. The cells of claim 1 wherein said cells are selected from the group consisting of mammalian cells, yeast and insect cells.

13. A method for synthesizing procollagen or collagen in recombinant eukaryotic host cells comprising:

transfecting at least one human procollagen or collagen gene encoding at least one polypeptide chain selected from the group consisting of human type I collagen or procollagen, human type II collagen or procollagen, and human type III collagen or procollagen into cells;

transfecting a gene encoding prolyl 4-hydroxylase or a subunit of prolyl 4-hydroxylase into said cells;

culturing said cells under conditions such that said transfected procollagen or collagen genes are expressed; and selecting transgected cells that comprise at least one molecule derived from said procollagen or collagen or genes.

14. The method of claim 13 wherein one of said transfected human procollagen genes is the COL1A1 gene encoding the proα1 (I) Chain of human type I procollagen.

15. The method of claim 14 further comprising the step of transfecting the host cell with the COL1A2 gene encoding the proα2 (I) chain of human type I procollagen.

16. The method of claim 13 wherein one of said transfected human procollagen genes is the COL2A1 gene encoding the proα1(II) chain of human type II procollagen.

17. The method of claim 13 wherein one of said transfected human procollagen genes is the COL3A1 gene encoding the proα1 (III) chain of human type III procollagen.

18. The method of claim 13 wherein said collagen or procollagen comprises at least one collagenase recognition site.

19. The method of claim 13 wherein said recombinant host cells are non-human mammalian cells.

20. The method of claim 13 wherein said recombinant cells are insect cells.

21. The method of claim 13 wherein said recombinant host cells are yeast cells.

22. The method of claim 13 wherein the recombinant eukaryotic host cells are selected from the group comprising mammalian cells, yeast and insect cells.

23. The method of claim 21 wherein said recombinant host cells are *Saccharomyces cervisiae*.

* * * * *

UNITED STATES PATENT AND TRADEMARK OFFICE
CERTIFICATE OF CORRECTION

PATENT NO.   : 5,593,859  
DATED        : January 14, 1997  
INVENTOR(S)  : Prockop et al.

It is certified that error appears in the above-identified patent and that said Letters Patent is hereby corrected as shown below:

<u>Title page,</u>  
Item [73], Assignee, after "Philapelphia, PA" please insert -- FibroGen, Inc., South San Francisco, CA --

Signed and Sealed this

Second Day of July, 2002

*Attest:*

*Attesting Officer*

JAMES E. ROGAN  
*Director of the United States Patent and Trademark Office*

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:1:

Arg Thr His Asp
    1

( 2 ) INFORMATION FOR SEQ ID NO:2:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear     ( i i ) MOLECULE TYPE: DNA (genomic)

( i x ) FEATURE:
        ( A ) NAME/KEY: CDS
        ( B ) LOCATION: 1..12

( x i ) SEQUENCE DESCRIPTION: SEQ ID NO:2:

AGG TAC CAT GAC                        12
Arg Tyr His Asp
1

( 2 ) INFORMATION FOR SEQ ID NO:3:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:3:

```
Phe  Pro  Gly  Ala
 1
```

( 2 ) INFORMATION FOR SEQ ID NO:4:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:4:

```
Leu  Pro  Gly  Pro
 1
```

( 2 ) INFORMATION FOR SEQ ID NO:5:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear     ( i i ) MOLECULE TYPE: DNA (genomic)

( i x ) FEATURE:
        ( A ) NAME/KEY: CDS
        ( B ) LOCATION: 1..12

( x i ) SEQUENCE DESCRIPTION: SEQ ID NO:5:

```
CTC  CCT  GGT  CCT                                                    12
Leu  Pro  Gly  Pro
 1
```

( 2 ) INFORMATION FOR SEQ ID NO:6:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear     ( i i ) MOLECULE TYPE: DNA (genomic)

( i x ) FEATURE:
        ( A ) NAME/KEY: CDS
        ( B ) LOCATION: 1..12

( x i ) SEQUENCE DESCRIPTION: SEQ ID NO:6:

```
CTG  CCC  GGG  CCT                                                    12
Leu  Pro  Gly  Pro
 1
```

( 2 ) INFORMATION FOR SEQ ID NO:7:

( i ) SEQUENCE CHARACTERISTICS:
        ( A ) LENGTH: 4 amino acids
        ( B ) TYPE: amino acid
        ( C ) STRANDEDNESS: single ( D ) TOPOLOGY: linear ( i i ) MOLECULE TYPE: peptide ( x i ) SEQUENCE DESCRIPTION: SEQ ID NO:7:

Ala Ala Gly Arg
1